(12) United States Patent
Marshall et al.

(10) Patent No.: US 7,087,068 B1
(45) Date of Patent: Aug. 8, 2006

(54) LANCET

(75) Inventors: Jeremy Marshall, Oxford (GB); Glenn Davison, Oxford (GB)

(73) Assignee: Owen Mumford Limited, Oxford (GB)

( * ) Notice: Subject to any disclaimer, the term of this patent is extended or adjusted under 35 U.S.C. 154(b) by 316 days.

(21) Appl. No.: 10/049,852

(22) PCT Filed: Aug. 21, 2001

(86) PCT No.: PCT/GB00/03222

§ 371 (c)(1),
(2), (4) Date: Feb. 19, 2002

(87) PCT Pub. No.: WO01/13794

PCT Pub. Date: Mar. 1, 2001

(30) Foreign Application Priority Data

Aug. 19, 1999 (GB) .................................. 9919681.8

(51) Int. Cl.
*A61B 17/34* (2006.01)
*A61B 5/151* (2006.01)
(52) U.S. Cl. ........................ 606/182; 606/181; 600/583
(58) Field of Classification Search ................. 606/167, 606/170, 181, 182, 184, 185
See application file for complete search history.

(56) References Cited

U.S. PATENT DOCUMENTS

| 4,895,147 | A |   | 1/1990  | Bodicky et al. |
|-----------|---|---|---------|---------------------------|
| 5,318,584 | A | * | 6/1994  | Lange et al. ...... 606/182 |
| 5,569,189 | A | * | 10/1996 | Parsons ............. 604/68 |
| 5,871,494 | A | * | 2/1999  | Simons et al. ..... 606/181 |
| 6,045,567 | A | * | 4/2000  | Taylor et al. ...... 606/181 |

* cited by examiner

*Primary Examiner*—Julian W. Woo
*Assistant Examiner*—Sarah Webb
(74) *Attorney, Agent, or Firm*—Young & Thompson

(57) ABSTRACT

A skin pricker has a barrel (1,11) in which a hammer (2,29) released by a trigger mechanism (32,34) can be shot forwards by a compressed spring (3,38) to impact on a lancet (24) and momentarily project its tip. The rear end of the spring acts against a barrier (4,39) adjustable axially of the barrel, so that the spring can be more or less compressed before release, causing the hammer to act with greater or lesser force on the lancet. The barrier (4,39) may have projections (6,8,42) that engage in skew slots (7,9,43) in the barrel, so that rotation of the barrier axially adjusts it. A sleeve (44) over the rear part of the barrel instrumental in priming the device may co-operate with the projections and be rotatable to set the desired spring force.

8 Claims, 3 Drawing Sheets

LANCET

BACKGROUND OF THE INVENTION

This invention relates to medical skin piercing devices.

DESCRIPTION OF THE RELATED ART

Many skin prickers have a spring-operated mechanism that projects the tip of a lancet from a leading end of a barrel. The device is held against the user's skin and "fired".

Usually the springs have a set rate and the force with which the lancet is urged forwards is always the same for the particular device in question. But that is not ideal. For example some skins can be very tough, while others, particularly of infants, can be very soft and easily pierced. Therefore it is desirable to have available devices which can cope with such variations.

SUMMARY OF THE INVENTION

According to the present invention, there is provided a medical skin piercing device comprising a barrel, means for carrying a lancet in the forward part of the barrel to allow the tip of the lancet to advance from a retracted to a projection position, a hammer arranged when released from a rearward position to act on the rear of the lancet to cause such advance, a barrier to the rear of the hammer and adjustable axially within the barrel by cam action as a result of rotation, a spring acting between the barrier and the hammer, and a trigger mechanism for holding the hammer in, and releasing it from, said rearward position with the spring compressed to a degree determined by the axial adjustment of the barrier.

Conveniently, the barrel has slots skew to the axis of the barrel in which projections on the barrier engage. The slots may have short portions non-skew to said axis to locate the projections in set positions. These projections may be on resilient formations integral with the barrier, allowing the projections to be moved radially inwards for insertion of the barrier into the barrel, the projections springing outwardly when they register with the slots.

Preferably, the rear portion of the barrel is encased by a captive sleeve spring urged forwardly, the sleeve having a lost motion connection through the rear end of the barrel and through the barrier to the hammer, whereby pulling back the sleeve retracts the hammer to said rearward position, and release of the sleeve allows the sleeve to revert to its forward position disconnected from the hammer. The sleeve when pulled back may reveal the slots for adjustment of the projections in the slots, but preferably it will co-operate with at least one said projection and be rotatable to adjust the barrier.

A nose section of the barrel will conveniently be removable to expose the lancet carrying means and allow lancets to be removed and replaced. These lancet carrying means may be a generally tubular member with limited axial movement, into which a lancet fits from the forward end and spring urged rearwardly normally to maintain a lancet tip retracted.

To avoid handling a lancet after use, an ejector rod can extend lengthwise of the barrel through the barrier and the hammer and be movable forwards to eject a lancet from the carrying means when the nose section is removed.

For a better understanding of the invention some embodiments will now be described, by way of example, with reference to the accompanying drawings, in which:

FIG. 1 is a diagrammatic side view, partly in section and partly in ghost, of a device for adjusting the penetration force of a medical needle or lancet, set to a maximum, FIG. 2 is a cross-section on the line II—II of FIG. 1, FIG. 3 is a side view similar to FIG. 1 but with the device set to a minimum, FIG. 4 is a cross-section on the line IV—IV of FIG. 3, FIG. 5 is a development of a curved slot in the barrel of the device.

Figure 1:
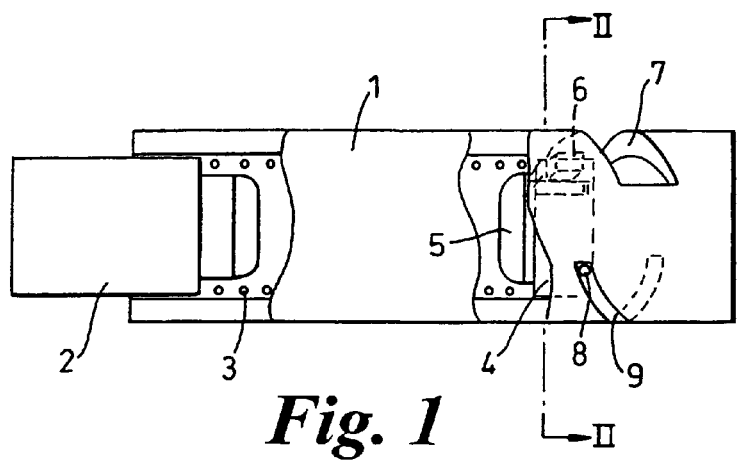
Figure 2:
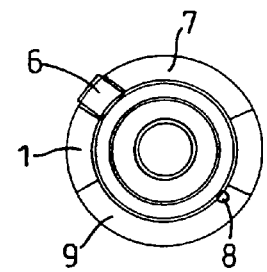
Figure 3:
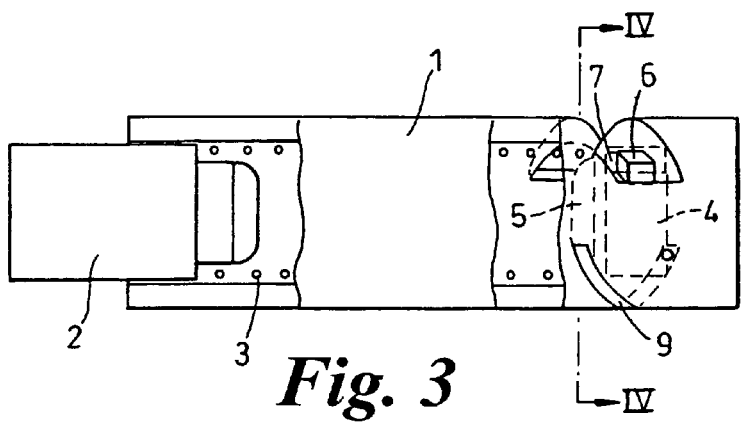
Figure 4:
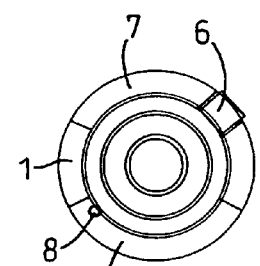

The device of FIG. 1 has a barrel 1 with a hammer 2 loosely plugging its forward end and urged forwards by a spring 3. There is a trigger mechanism (not shown) which holds the hammer 2 in the cocked position shown. The spring 3 reacts against an axially adjustable barrier 4 towards the rear end and when the trigger is operated it shoots the released hammer 2 forwards.

The barrier 4 is of thick, disc-like form with a protuberance 5 on its forward side around which the spring locates. The cylindrical surface of the disc, of a radius slightly less than the inner radius of the barrel, has two diametrically opposed projections, one being a cam 6 which projects into a part-helical slot 7 in the barrel and the other being a small stud 8 which co-operates with a part-helical slot 9 complementary to the slot 7.

Figure 5:
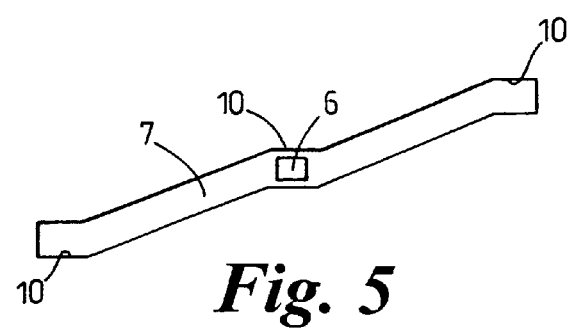
Figure 6:
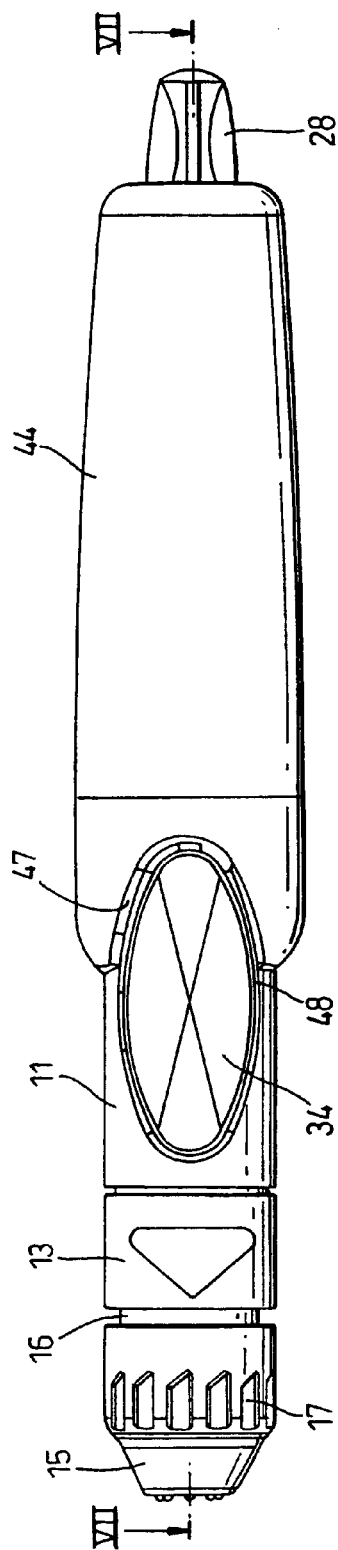
FIG. 6 is a side view of a skin pricker.
Figure 7:
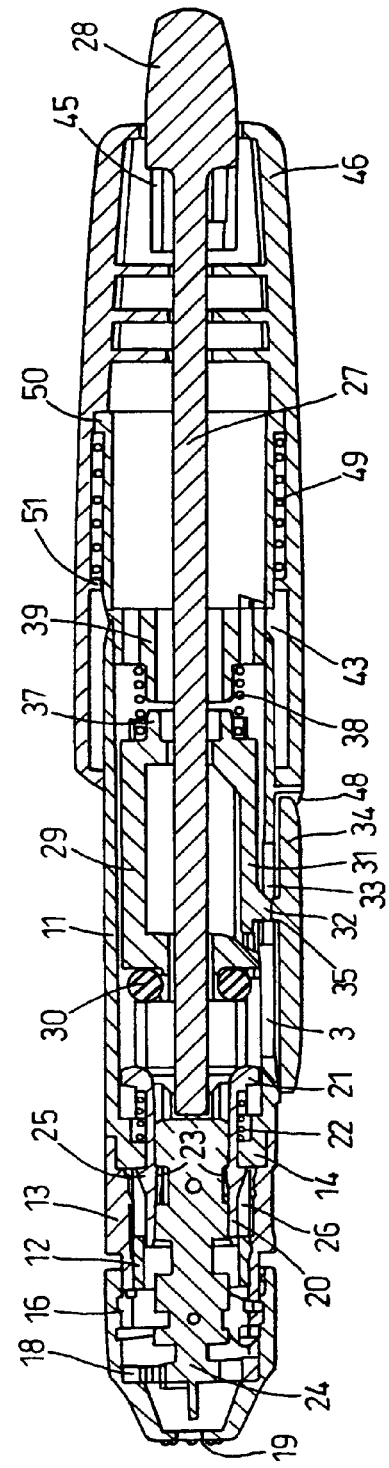
FIG. 7 is a longitudinal section of the skin pricker, on the line VII—VII of FIG. 6.

The slots 7 and 9 are not smooth sided over their whole lengths. At their ends and at their mid-points they divert into flats 10 normal rather than skew to the axis of the barrel. This enables the cam 6 and stud 8 to locate stably at three set positions, the extreme ones being shown in FIGS. 1 to 4 and the intermediate one in FIG. 5. It would be possible to have more than one intermediate position.

The barrel 1 is of moulded plastics, giving some elasticity and resilience. This enables the barrier 4 to be pressed into place through the rear end of the barrel. It may be convenient to push it in aslant, with the cam 6 leading, and skew to correspond to the angle of the slot 7. Then the cam 6 can be worked up, with the adjacent portion of the barrier 4, into the slot 7, followed by the portion adjacent the stud 8 being pushed until the stud registers with the slot 9. The barrier is then manipulated until it is co-axial with the barrel 1. It will be kept substantially square on to the axis by the spring 1, by the cam 6 in the slot 7 and the stud 8 in the slot 9, and by the co-operation of its cylindrical end surface with the inner surface of the barrel (which will have reverted to its proper shape following any distortion suffered as a result of inserting the barrier).

The cam 6 is accessible, and the user can shift it along the slot 7 to cause the barrier 4 to increase or decrease the compression of the spring 3. When the barrier is forwards, as in FIG. 1, there is maximum initial compression, and the hammer 2 is propelled forwards with maximum force. Correspondingly, when the barrier is rearwards, as in FIG. 3, the hammer is propelled forwards with lesser force.

A practical example is shown in FIGS. 6 to 9 in which a skin pricker has a cylindrical barrel 11 with a reduced forward end portion 12 over which fits a connecting collar 13, screwing to the barrel at shoulder 14. A nose piece 15 attaches to the collar 13, being fitted over a reduced forward end portion 16 before being trapped by a non-return formation. But although captive, it can still be rotated, using grip 17, to adjust its axial position within limits. An internal ring 18 determines this, and thereby controls the amount by which a lancet tip will project through aperture 19.

The barrel portion 12 receives and guides a tubular lancet holder 20 whose rear out-turned rim 21 is initially held back from the shoulder 14 by a light spring 22. At about its mid-length the holder has shallow internal projections 23 which retain a lancet 24 snapped in from the front end, and more pronounced external barbs 25 which snap into slots 26 in the portion 12 from the rear, allowing limited axial travel of the holder 20. Initially, the tip of the lancet 23 is retracted within the nose piece 15.

An ejector rod 27 extends co-axially through the barrel and beyond to the rear, and when the collar 13, with the nose piece 15, is removed it can be pressed by rear end knob 28 to snap the lancet forwardly out of the holder 20.

A hammer 29 has a generally cylindrical hollow body through which the rod 27 freely passes, and with a cylindrical spigot at its forward end around which snaps a rubber ring 30. When released, this will hit the rim 21 to drive the holder 20 and thus the lancet forwards. This ring device serves as a damper and the rubber ensures virtually silent operation. A narrow U-shaped slot in the cylindrical wall of the hammer forms a flexible finger 31 which, at its free forward end, has an outwardly projecting stud 32 engaged in a slot 33 in the barrel. This is part of a trigger mechanism, whose other part is an oval button 34 mounted over this region of the barrel and with an inner projection 35 that co-operates with the stud 32. Pressure on the button flexes the finger 31 in to release the stud 32 from the slot 33 and allows the hammer to shoot forwards. The finger 31 can almost immediately recover its original attitude with the stud 32 entering another slot 36.

At its rear end, the hammer 29 has a short cylindrical extension 37 which locates the forward end of a helical drive spring 38, whose rear end reacts against a force adjuster 39.

Figure 8:
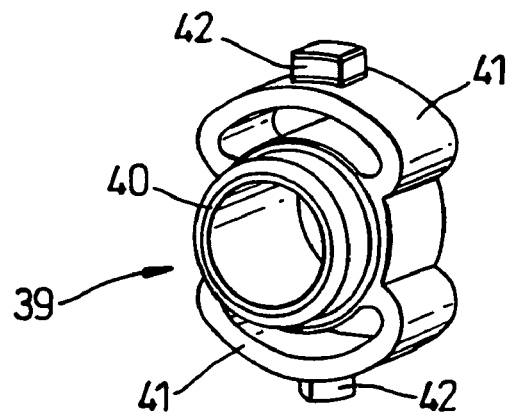
FIG. 8 is a perspective view of a spring force adjuster forming part of the pricker of FIG. 6.
Figure 9:
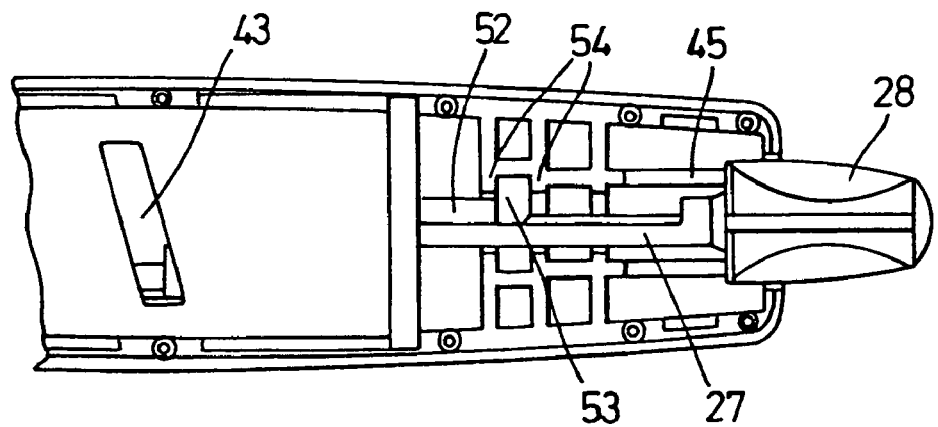
FIG. 9 is a longitudinal section of the rear portion of the pricker of FIG. 6, the sectional plane being at right angles to that of FIG. 7.

The force adjuster is best seen in FIG. 8. It has a cylindrical plastics body 40, through which the rod 27 will freely pass, and on the outside of that two diametrically opposed integral loops 41 of arcuate form, each subtending an angle of about 90°. The outer surfaces of the loops are of a radius corresponding to the interior of the barrel 11 but the loops are thin enough to be deformed radially inwards, to allow outwardly projecting studs 42 at the centres of those outer surfaces to be depressed sufficiently to enable the adjuster to be entered into the rear of the barrel. When the studs reach opposed inclined slots 43 in the barrel the loops 41 spring outwards, and the studs are captive.

A sleeve 44 sheaths the rear end of the barrel 11 and provides at its rear end a guide slot 45 for the knob 28 of the rod 27.

The sleeve 44 is made from two substantially semi-cylindrical halves, one half 46 having at its leading end a recess 47 matching in shape the rear part of a low wall 48 proud of the barrel 11 and closely surrounding the trigger button 34. The sleeve 44 is urged forwards by a helical spring 49 around the barrel, acting between a rear end flange 50 on the barrel and an annular rib 51 internal of the sleeve. Normally, the spring 49 causes the sleeve 44 to be located with the wall 48 nesting in the recess 47.

The ejector rod 27 is reduced to semi-circular cross-section over much of its length and along this portion lies a complementarily shaped, shorter, loading rod 52 with a certain freedom of axial movement relative to the rod 27. This has a rear end head 53 which is trapped by internal webs 54 of the sleeve 44 and it passes through the force adjuster 39 into the hammer 29, where barbs or spring fingers engage the rear wall of the hammer. Initially, both the hammer 29 and the sleeve 44 are in their forward positions. But once the lancet has been loaded, the sleeve 44 is pulled back, and the loading rod 52, drawn by its head 53, pulls back the hammer 29, the stud 32 being temporarily pressed inwards by the bridge between the slots 33 and 36. Then the hammer is trapped in its rearward ready-to-fire position and the sleeve 44 can be allowed to spring forwards, taking the rod 52 with it and freeing the hammer 29 for forward movement.

When the sleeve 44 is in its rearward position, it can be rotated to operate the force adjuster 39, being turned one way to move the adjuster forwards and increase the initial spring force, and the other way to move the adjuster rearwardly and reduce that initial force. At least one of the studs 42 will be proud of the barrel 11 and can be positively engaged by a formation within the forward end of the sleeve, behind inturned rib 55. The amount of force adjustment can be gauged by the amount of rotation. Once the sleeve is released to spring forwards, it is guided into its original alignment by the recess 47 meeting the wall 48.

The sleeve 44 could be arranged to expose at least one of the studs 42, so that the user could directly manipulate the force adjuster. But that might prove awkward in practice.

In these figures the slots in the barrel are shown without flats, but their angle is such that the studs will remain where positioned by friction. But flats could be provided if desired.

The invention claimed is:

1. A medical skin piercing device comprising a barrel, means for carrying a lancet in the forward part of the barrel to allow the tip of the lancet to advance from a retracted to a projecting position, a hammer arranged when released from a rearward position to impact on the rear of the lancet to cause such advance, a barrier to the rear of the hammer and user-adjustable axially within the barrel by cam action as a result of rotation of the barrier, a spring acting between the barrier and the hammer, and a trigger mechanism for holding the hammer in and releasing the hammer from said rearward position with the spring compressed to a degree determined by the axial adjustment of the barrier, wherein the user-set degree of compression of the spring determines the force propelling the hammer after release of the hammer, wherein the barrel has slots skew to the axis of the barrel in which projections on the barrier engage, wherein the rear portion of the barrel is encased by a captive sleeve spring-urged forwardly, the sleeve having a lost motion connection through the rear end of the barrel and through the barrier to the hammer, whereby pulling back the sleeve retracts the hammer to said rearward position, and release of the sleeve allows the sleeve to revert to its forward position disconnected from the hammer, and wherein the sleeve when pulled back reveals the slots for adjustment of the projections in the slots.

2. A device as claimed in claim 1, wherein the slots have short portions non-skew to said axis to locate the projections in set positions.

3. A device as claimed in claim 1, wherein the projections are on resilient formations integral with the barrier, allowing the projections to be moved radially inwards for insertion of the barrier into the barrel, the projections springing outwardly when they register with the slots.

4. A device as claimed in claim 1, wherein a nose section of the barrel is removable to expose the lancet carrying means and allow lancets to be removed and replaced.

5. A medical skin piercing device, comprising a barrel, means for carrying a lancet in the forward part of the barrel to allow the tip of the lancet to advance from a retracted to a projecting position, a hammer arranged when released from a rearward position to impact on the rear of the lancet to cause such advance, a barrier to the rear of the hammer and user-adjustable axially within the barrel by cam action as a result of rotation of the barrier, a spring acting between the barrier and the hammer, and a trigger mechanism for holding the hammer in and releasing the hammer from said rearward position with the spring compressed to a degree determined by the axial adjustment of the barrier, wherein the user-set degree of compression of the spring determines the force propelling the hammer after release of the hammer, wherein the barrel has slots skew to the axis of the barrel in which projections on the barrier engage, wherein the rear portion of the barrel is encased by a captive sleeve spring-urged forwardly, the sleeve having a lost motion connection through the rear end of the barrel and through the barrier to the hammer, whereby pulling back the sleeve retracts the hammer to said rearward position, and release of the sleeve allows the sleeve to revert to its forward position disconnected from the hammer, and wherein the sleeve when pulled back co-operates with at least one said projection and is rotatable to adjust the barrier.

6. A device as claimed in claim 5, wherein the slots have short portions non-skew to said axis to locate the projections in set positions.

7. A device as claimed in claim 5, wherein the projections are on resilient formations integral with the barrier, allowing the projections to be moved radially inwards for insertion of the barrier into the barrel, the projections springing outwardly when they register with the slots.

8. A medical skin piercing device comprising a barrel, means for carrying a lancet in the forward part of the barrel to allow the tip of the lancet to advance from a retracted to a projecting position, a hammer arranged when released from a rearward position to impact on the rear of the lancet to cause such advance, a barrier to the rear of the hammer and user-adjustable axially within the barrel by cam action as a result of rotation of the barrier, a spring acting between the barrier and the hammer, and a trigger mechanism for holding the hammer in and releasing the hammer from said rearward position with the spring compressed to a degree determined by the axial adjustment of the barrier, wherein the user-set degree of compression of the spring determines the force propelling the hammer after release of the hammer, wherein a nose section of the barrel is removable to expose the lancet carrying means and allow lancets to be removed and replaced, wherein the lancet carrying means is a generally tubular member with limited axial movement, into which a lancet fits from the forward end and spring-urged rearwardly normally to maintain a lancet tip retracted, and wherein an ejector rod extends lengthwise of the barrel through the barrier and the hammer and is movable forwards to eject a lancet from the carrying means when the nose section is removed.

* * * * *

UNITED STATES PATENT AND TRADEMARK OFFICE
CERTIFICATE OF CORRECTION

PATENT NO. : 7,087,068 B1 Page 1 of 1
APPLICATION NO. : 10/049852
DATED : August 8, 2006
INVENTOR(S) : Jeremy Marshall et al.

It is certified that error appears in the above-identified patent and that said Letters Patent is hereby corrected as shown below:

On the title page, amend Item (22) to read as follows:
--(22) PCT Filed: Aug. 21, 2000--.

Signed and Sealed this

Fourteenth Day of November, 2006

JON W. DUDAS
*Director of the United States Patent and Trademark Office*